(12) United States Patent
Nooreddeen et al.

(10) Patent No.: US 11,684,507 B2
(45) Date of Patent: Jun. 27, 2023

(54) PEDIATRIC LITHOTOMY POSITIONING SPLINT

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Eman Nooreddeen, Riyadh (SA); Layla Adam Al Somaily, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 14 days.

(21) Appl. No.: 16/854,211

(22) Filed: Apr. 21, 2020

(65) Prior Publication Data
US 2021/0322199 A1    Oct. 21, 2021

(51) Int. Cl.
*A61F 5/058* (2006.01)
*A61F 5/37* (2006.01)
*A61F 5/01* (2006.01)

(52) U.S. Cl.
CPC ........ *A61F 5/0585* (2013.01); *A61F 5/05858* (2013.01); *A61F 5/373* (2013.01); *A61F 5/3753* (2013.01); *A61F 2005/0167* (2013.01)

(58) Field of Classification Search
CPC ........ A61F 5/01; A61F 5/0102; A61F 5/0127; A61F 5/0104; A61F 5/0123;
(Continued)

(56) References Cited

U.S. PATENT DOCUMENTS

| | | | | |
|---|---|---|---|---|
| 2,935,984 A | * | 5/1960 | Kerr | A61F 5/0193 99/421 A |
| 3,068,862 A | * | 12/1962 | Fuzere | A61F 5/0193 602/24 |

(Continued)

FOREIGN PATENT DOCUMENTS

| | | |
|---|---|---|
| CN | 2722867 Y | 9/2005 |
| CN | 206424185 U | 8/2017 |
| CN | 207734398 U | 8/2018 |

OTHER PUBLICATIONS

Article entiteld, "How Does a Hip Joint Move?"[retrieved Nov. 16, 2021]; Retrieved from website entitled, "Brainlab Org", using internet URL https://www.brainlab.org/get-educated/hip/hip-anatomy/how-does-your-hip-joint-move/ (Year: 2021).*

(Continued)

*Primary Examiner* — Ophelia A Hawthorne
*Assistant Examiner* — Gina McCarthy
(74) *Attorney, Agent, or Firm* — Oblon, McClelland, Maier & Neustadt, L.L.P.

(57) ABSTRACT

A positioning splint for safely and securely positioning a pediatric patient into a lithotomy position. The splint comprises a toroid, wedge-shaped splint having an anterior and posterior jaw which is attached to shoulder straps or a jacket/vest that holds the splint in place during use. The wedge splint and shoulder attachments are padded. The wedge splint may have a disposable covering. Methods of using the splint to position a patient for urinary catheterization as well as for other procedures, exams and surgeries requiring unobstructed access to the perineal and anorectal areas. Additional wrist/hand and ankle/leg straps are used for conscious patients who are uncooperative or incompetent patients or in the case of a patient with involuntary movement disorders.

12 Claims, 21 Drawing Sheets

(58) Field of Classification Search
CPC .. A61F 5/0193; A61F 5/04; A61F 5/05; A61F 5/058; A61F 5/05825; A61F 5/05841; A61F 5/0585; A61F 5/05858; A61F 5/3753; A61F 2005/0167; A61F 5/3972; A61G 13/123; A61B 17/6441
See application file for complete search history.

(56) References Cited

U.S. PATENT DOCUMENTS

| | | | | |
|---|---|---|---|---|
| 4,393,865 | A * | 7/1983 | Lambert | A61F 5/0193 602/24 |
| 4,913,136 | A * | 4/1990 | Chong | A61F 5/0193 602/24 |
| 2004/0244114 | A1 * | 12/2004 | Robinette | A61F 5/3784 5/626 |
| 2013/0306081 | A1 | 11/2013 | Devapatla et al. | |

OTHER PUBLICATIONS

"Hip Dysplasia Brace Sleeve", Pelican Manufacturing, https://www.pelicanmanufacturing.com.au/product/hip-dysplasia-brace-sleeve/, Aug. 1, 2019, 3 pages.

Paula Curry, "Breastfeeding with a Pavlik Harness / Hip Dysplasia", Thruparenting, https://thruparenting.com/breastfeeding-with-a-pavlik-harness-hip-dysplasia/, May 12, 2019, 9 pages.

* cited by examiner

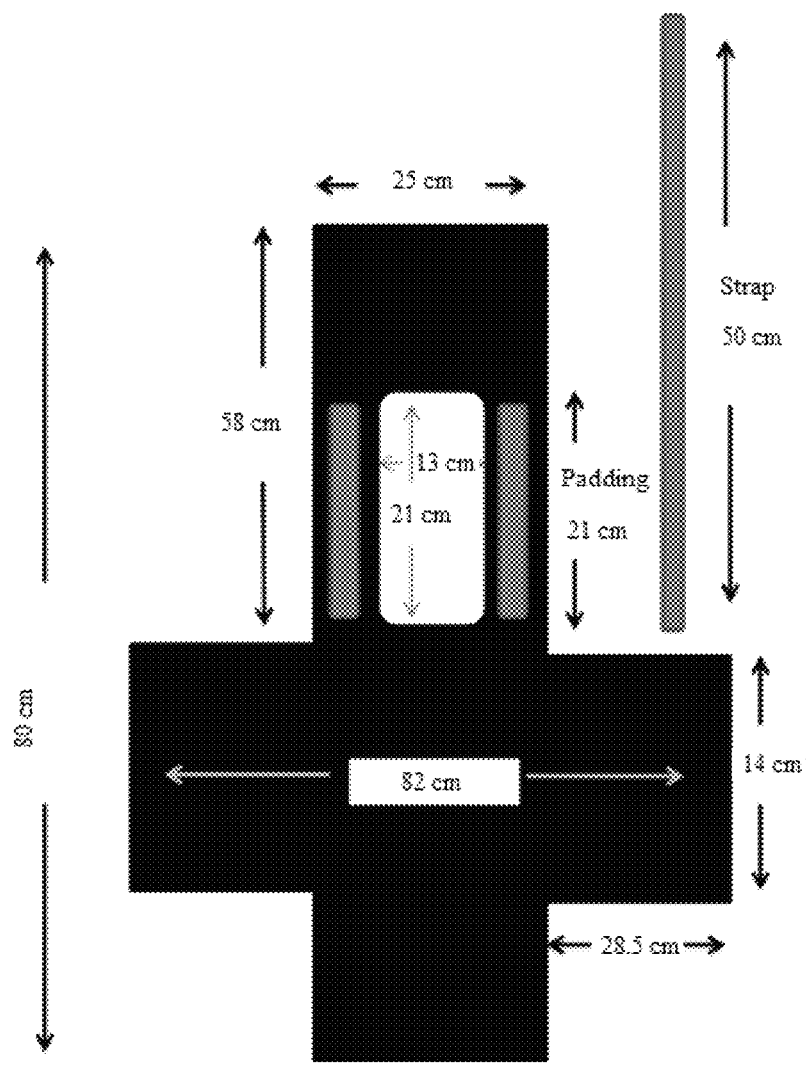
Figure 15-B

PEDIATRIC LITHOTOMY POSITIONING SPLINT

BACKGROUND OF THE INVENTION

Field of the Invention

The invention relates to a medical device that positions a patient in a lithotomy position to perform procedures in pediatric medicine.

Description of Related Art

In urinary catheterization, a latex, polyurethane, or silicone tube known as a urinary catheter is inserted into a patient's bladder via the urethra. Catheterization allows the patient's urine to drain freely from the bladder for collection and can also be used to inject liquids used for treatment or diagnosis of bladder conditions. Usually, a clinician, often a nurse, performs the procedure, but self-catheterization is also possible.

The catheter may be a permanent or indwelling catheter or an intermittent catheter removed after each catheterization. Intermittent catheterization means removing urine from the bladder by placing a tube into the bladder and is often done when children or adults are unable to empty the bladder on their own or when very high pressures have developed inside the bladder. Catheterization permits direct drainage of the urinary bladder and is often performed in pediatric practice.

Catheterization may be used for diagnostic purposes, such as for collection of an uncontaminated urine specimen for culture and urinalysis, for example, when it is essential to obtain a urine specimen from a young child who cannot void on command. Urethral catheterization also may be performed to carry out cystourethrography or to monitor urine output in certain postoperative patients or very ill patients.

It is often necessary to restrain a young child during catheterization. However, improper or ineffective restraint may lead to multiple medical problems including contamination and infection of the urethra, injury to the patient, or failure of the catheterization.

Conventional restraints for children include applying straps to both wrists and ankles and pinning the straps to the bed using safety pins to extend and immobilize the upper and lower limbs or placing a cloth or baby diaper across both thighs in an extended and adducted position at the hips, putting a cloth tape over the cloth or baby diaper, and sticking it to either side of the bed; placing the child on a hard plastic mold in the shape of an infant and securing their extremities with hook and loop fasteners during circumcision; or putting a strip of hook and loop fasteners across the forehead, chest, and thighs during transport.

The normal posture of a child is a result of the muscular tone of the individual. The normal posture of a full term neonate is flexion at the elbow with external rotation of the arms and abduction and external rotation of the thighs with mild flexion at the hip joint, commonly referred to as the "frog leg posture". This frog leg posture allows the normal postnatal development of the acetabulum by deepening of the socket and growth of the labrum.

Neonatal medical procedures may take anywhere from a few minutes to couple of hours, therefore it is very important to restrain the neonates in their normal posture during this time to prevent injury or abnormal development. However, positioning, restraining, or holding of the neonate in adduction and extension at the hip joint leads to eversion of the labrum and elongation of the ligamentum teres which prevents the normal ossification of the acetabulum. Tight swaddling and other conventional methods of neonatal restraint also position the neonate in this undesirable abnormal position. Methods for positioning an infant for circumcision also suffer from a variety of problems, including permanent staining of the restraint device, the risk of contamination and infection, positioning, restraining, or holding a fragile neonate on a hard surface, and inability to place an infant in a safe and convenient position to offer routine care to the neonate. Thus, above-mentioned conventional techniques are not baby-friendly and some predispose a neonate to developmental dysplasia of the hip joints as well as infection. Various restraints have been proposed for infants but all suffer significant drawbacks.

U.S. Pat. No. 4,027,869, entitled "Patient Restraint for X-ray Studies of Infants", discloses an apparatus to immobilize an infant, particularly in connection with medical studies, such as x-ray studies, requiring a frog leg position. However, the apparatus is not baby-friendly because the straps are coupled to a rigid board which is placed under the infant and would be very uncomfortable for the infant for an extended period of time during a surgical procedure or transport of the infant. In addition, the device does not restrain the upper limbs.

U.S. Pat. No. 5,329,934, entitled "Medical Patient Restraint Device", discloses a device for restraining patients during surgical procedures such as the circumcision of infants that places the infant in a spread-eagle position.

Urine-collection devices include those of CN207734398U which describes a multifunctional urine-collecting device which has a urethral catheter fixing device has that functions to hold and fix catheter to prevent the catheter from falling. US20130306081A1 describes a neonatal body restraint device for use with CPAP. CN206424185U discloses a herringbone brace with a urine-collecting device. CN2722867Y discloses a hip flexion abduction orthopedic device. Pelican Manufacturing (hypertext transfer protocol secure://www.pelicanmanufacturing-.com.au/product/hip-dysplasia-brace-sleeve/) describes a brace that keeps a baby's legs apart for treating hip dysplasia and Curry (hypertext transfer protocol secure://thruparenting.com/breastfeeding-with-a-pavlik-harness-hip-dysplasia/) describes a harness used in babies having hip dysplasia having shoulder, chest, and leg straps.

However, none of these devices provide a secure and convenient positioning and holding of a neonate in need of urinary catheterization. Consequently, this is an unmet need for a child-friendly, inexpensive, sanitary, and reusable restraint system that easily and quickly secures a child into a position for urinary catheterization so that this procedure may be accomplished safely without injury.

BRIEF SUMMARY OF THE INVENTION

The invention provides a safe and convenient splint designed to facilitate urinary catheterization of a pediatric patient and as a method of positioning, restraining, or holding a child using the splint during a urinary catheterization. The splint makes the procedure of urinary catheterization of a pediatric patient convenient for medical staff and trained caregivers and reduces the risk of iatrogenic injury to the child which often results from malpositioning the child during urinary catheterization when no splint is used or when other unsuitable means for immobilizing a child are used. The splint reduces the amount of time for performing the urinary catheterization and reduces the number of staff members needed to safely perform the procedure to one or two individuals. The splint can be manufactured and customized for pediatric patients having different body weights, builds, and sizes and preferably has a disposable sanitary or sterilizable covering.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 2 provides a right side view of the device wedge (toroidal splint) where 101 is the posterior jaw, 102 is the anterior jaw and 103-R is the angulated side of the wedge on the right side where patient's right thigh will be placed on.

FIG. 6 provides a flipped over view from the back side of the wedge where 101-B is the outer side of the posterior jaw. 103-R is the right angulated side of the wedge where patient's right thigh will be placed on and 103-L is the left angulated side of the wedge where patient's left thigh will be placed on.

FIG. 7 provides a downward view of the wedge where 101-A is the internal side of the posterior jaw where patient's back will rest over, 101-B is the outer side of the posterior jaw where the overhead jacket or shoulder straps will be connected to the wedge, 102 is the anterior jaw of the wedge, 103-R is the right angulated side of the wedge where patient's right thigh will be placed on and 103-L is the left angulated side of the wedge where patient's left thigh will be placed on.

FIG. 12-B provides an overview of the outer side of the overhead jacket. 201-F is the frontal part of the jacket that will be applied to patient's anterior trunk. 201-B is the back part of the jacket that patient's back will rest over. 202 is jacket gap to allow for patient's head and neck to get through the jacket. 203-R and 203-L are the jacket arms where 203-R is the right arm and 203-L is the left arm. 207 are the shoulder straps. 209-B are the hooks on the outer side of jacket shoulders to be used to secure shoulder straps at time of application of the device to a patient. 210 are the loops on the left jacket arm placed at two levels to use according to patient's body built to attach to the hook located on the right jacket arm which will then secure patients upper limbs in place.

FIG. 13-B provides a close view of the overhead jacket frontal part which shows adjusted folded length of the frontal part of the jacket labeled as 201-F-F. The adjustment of length will be according to patient's body build. 201-F-F is the part that will be applied over patient's frontal trunk and will be attached to the anterior jaw of the wedge via 207 which are the shoulder straps. Afterwards, 207 will finally be attached to 209-B which are the hooks on the outer side of jacket shoulders to secure the wedge to the patient.

FIG. 14-B provides a close view of the overhead jacket at the level of jacket arm where an open hand restraint is attached. 201-B is the back part of the jacket that patient's back will rest over. 202 is the overhead jacket gap to allow for patient's head and neck to get through the jacket. 205 is the open hand restraint. 206 is the hand restraint strap.

FIG. 15-B describes dimensions for one embodiment of the jacket/vest.

DETAILED DESCRIPTION OF THE INVENTION

Figure 1:
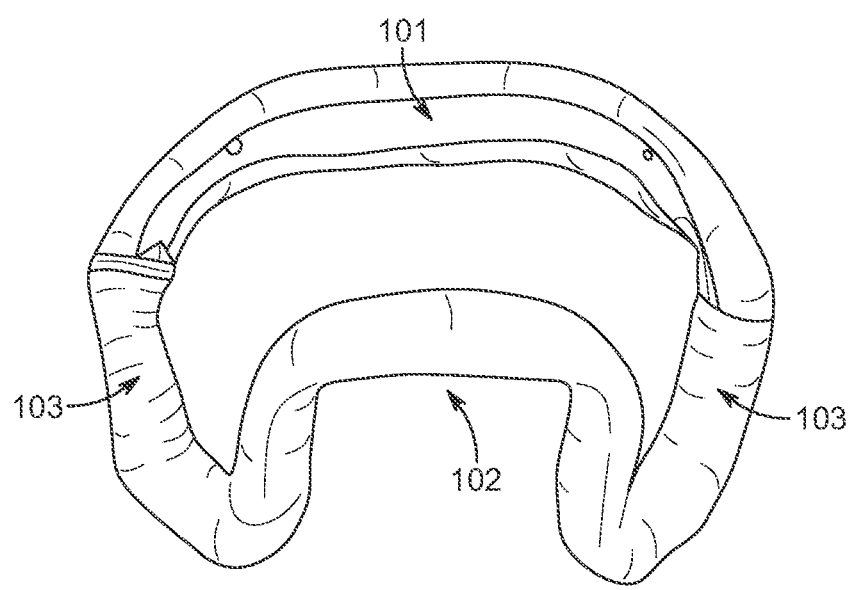
FIG. 1 Describes the basic components of the device wedge (toroidal splint) where 101 is the posterior jaw where patient's back will rest over, 102 is the anterior jaw and 103 is the angulated sides of the wedge where a patient's thighs will be placed.
Figure 2:
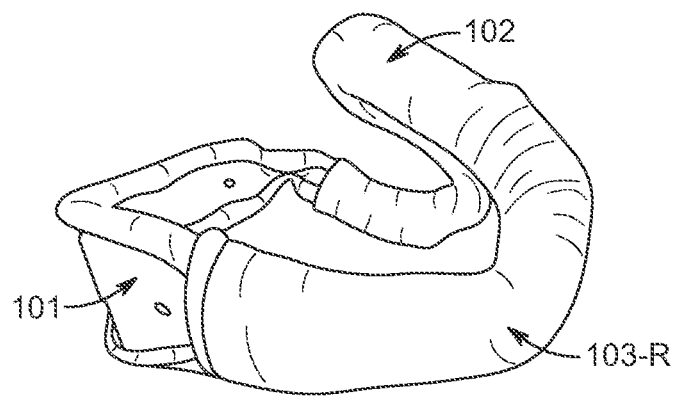
Figure 3:
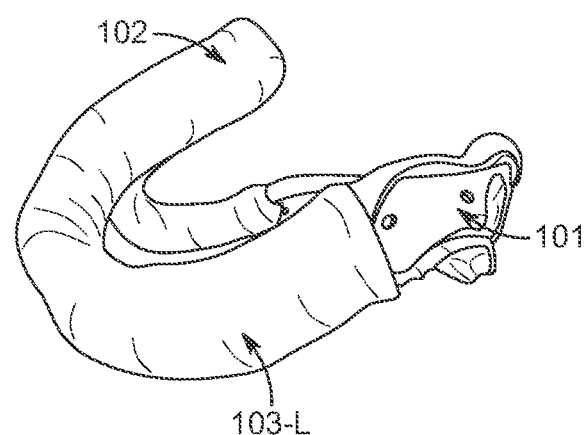
FIG. 3 provides a left side view of the device wedge (toroidal splint) where 101 is the posterior jaw, 102 is the anterior jaw and 103-L is the angulated side of the wedge on the left side where patient's left thigh will be placed.
Figure 4:
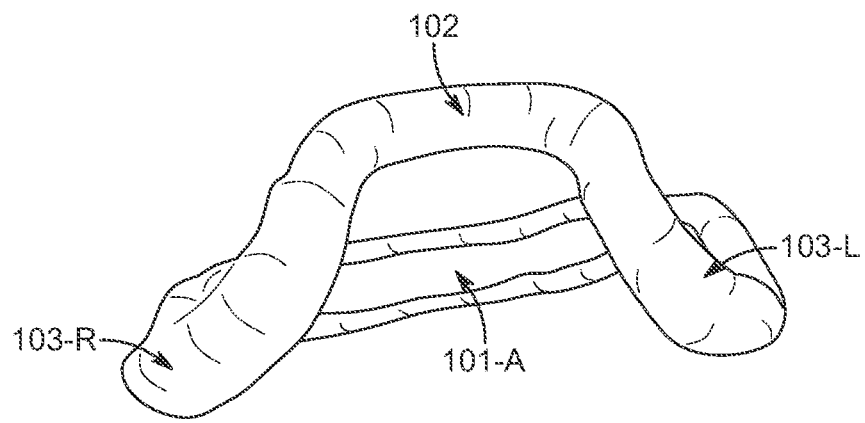
FIG. 4 provides a front view of the device wedge where 102 is the anterior jaw, 101-A is the internal side of the posterior jaw where patient's back will rest over. 103-R is the angulated side on the right where the right thigh will be placed and 103-L is the angulated side on the left where the left thigh will be placed.
Figure 5:
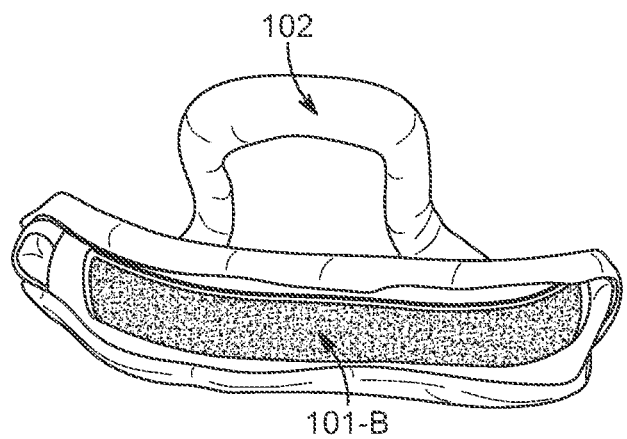
FIG. 5 provides an upright posterior view of the wedge where 101-B is the outer side of the posterior jaw and 102 is the anterior jaw of the wedge.
Figure 6:
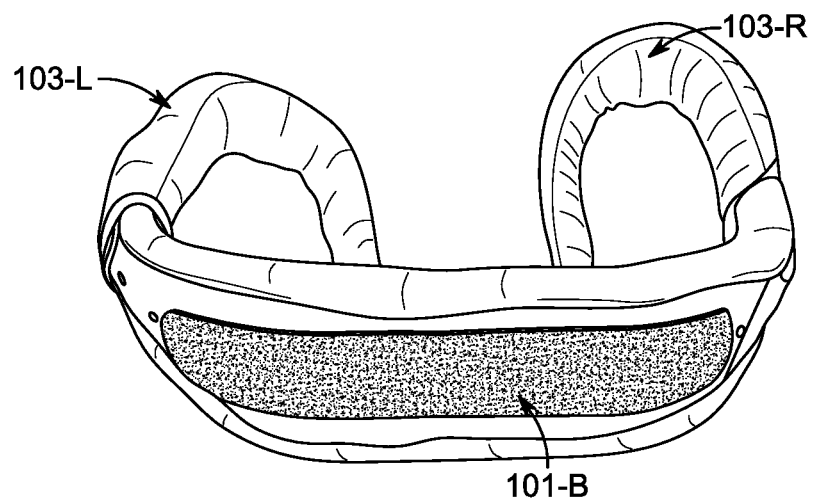
Figure 7:
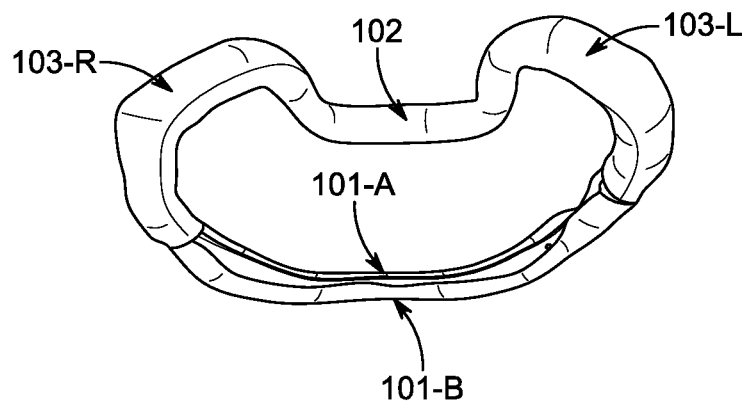
Figure 8:
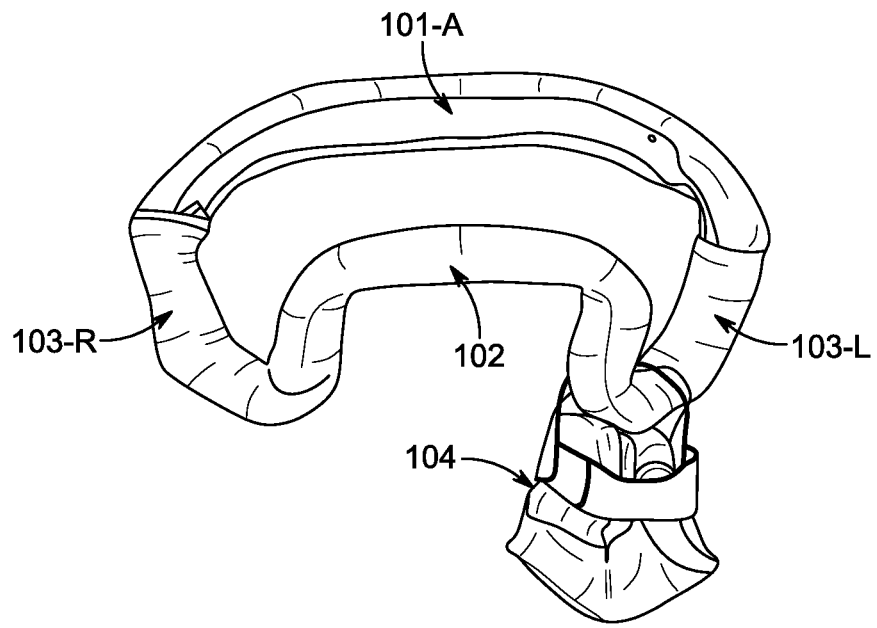
FIG. 8 an upward view of the wedge where 101-A is where patient's back will rest over, 102 is the anterior jaw of the wedge, 103-R is the right angulated side of the wedge where the right thigh will be placed on and 103-L is the angulated side on the left where the left thigh will be placed on. Attached to 103-L is 104 which is the left ankle restraint to demonstrate the placement of the ankle restraint into this embodiment to the angulated side of the wedge.
Figure 9:
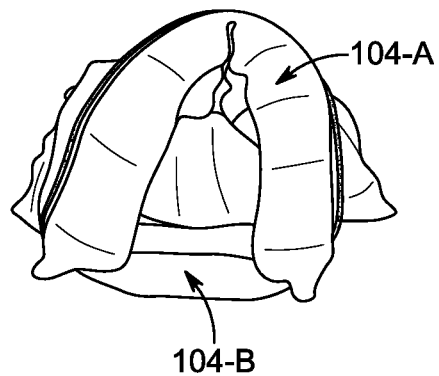
FIG. 9 shows the ankle restraint description where 104-A is the restraint body and 104-B is the restraint strap to secure the foot in place.
Figure 10:
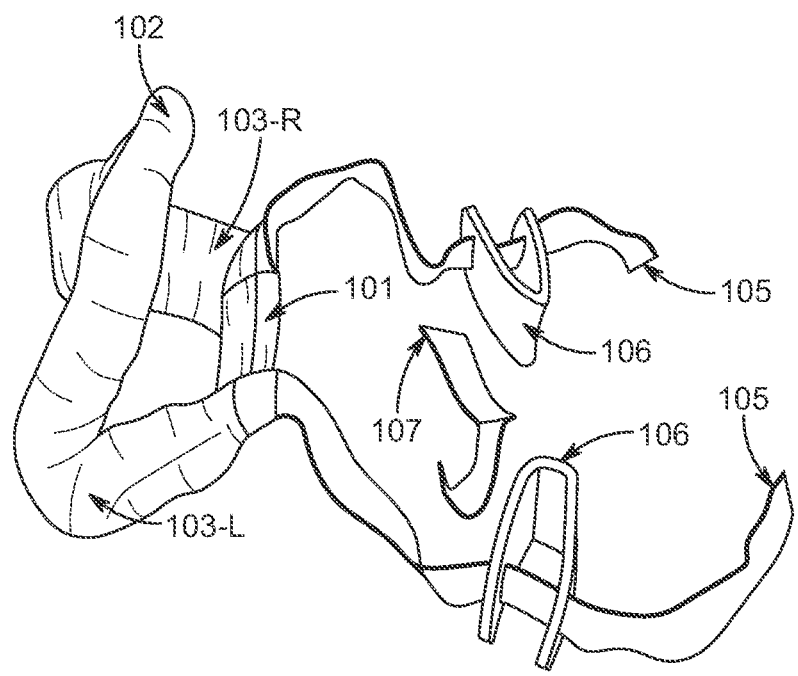
FIG. 10 is a description of the device wedge while attached to the shoulder straps where 101 is the posterior jaw of the wedge, 102 is the anterior jaw, 103-R is the right angulated side of the wedge where the right thigh will be placed on, 103-L is the angulated side on the left where the left thigh will be placed on, 105 is the shoulder straps attached to the posterior jaw of the wedge from one end and the other end is free to be later pulled over the shoulders from both sides and then looped around the anterior jaw (102) to be finally fixed to the anterior side of the straps to fix the wedge in place while it is applied to the patient during its use. Shoulder pads for comfort are labeled as 106. Hook pieces are labeled as 107 are used to secure the shoulder straps to it after they are passed over the anterior jaw of the wedge.
Figure 11:
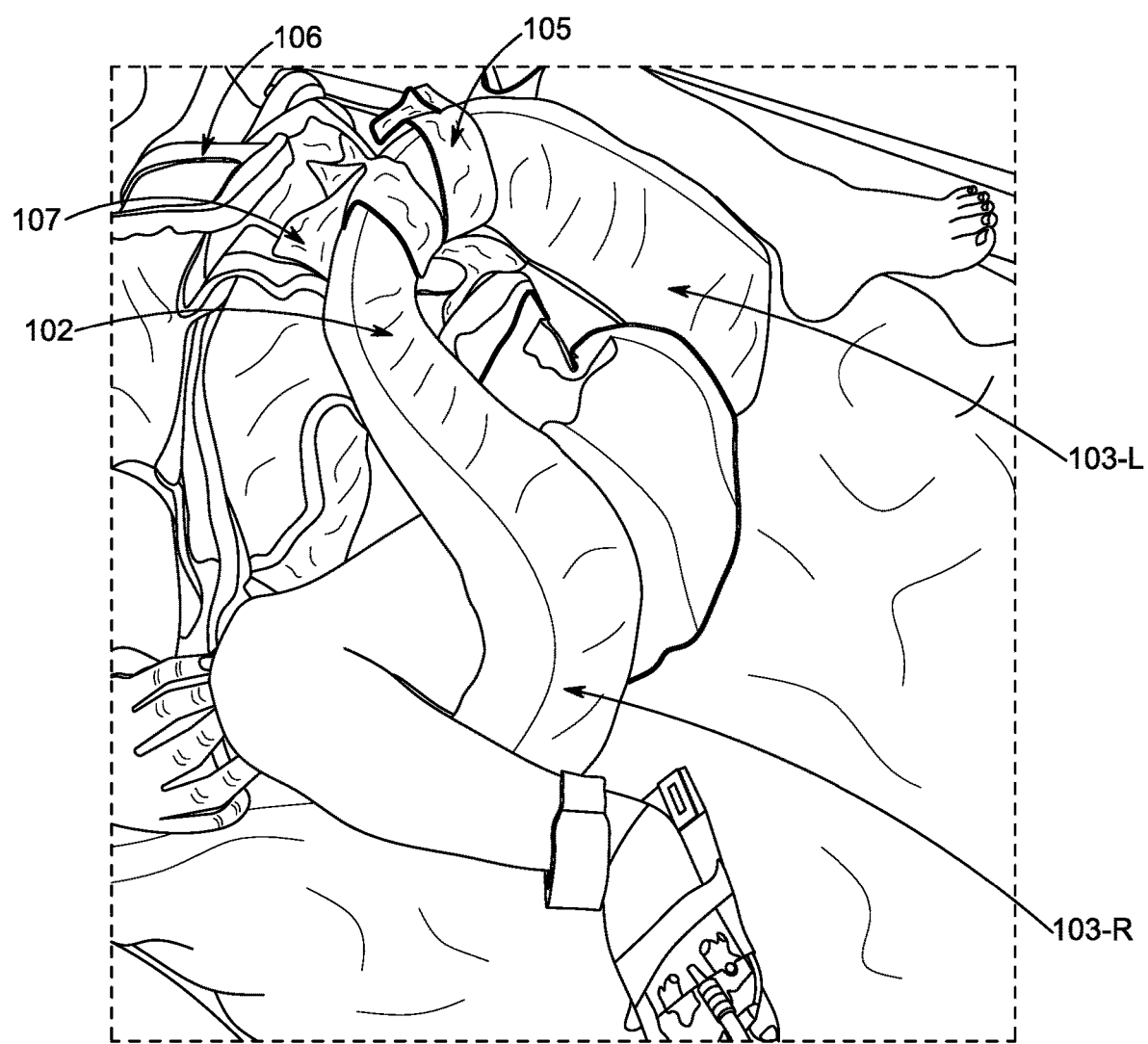
FIG. 11 provides a view of a pediatric patient placed in lithotomy position by the splint device described in FIG. 10 where 102 is the anterior jaw of the wedge, 103-R is the right angulated side of the wedge where the right thigh is placed on, 103-L is the left angulated side on the wedge where the left thigh is placed on. 105 is the shoulder straps that are attached in its back side to the posterior jaw of the wedge then extended over both shoulder which then are looped around the anterior jaw of the wedge and finally the anterior end of the straps are fixed to itself using hook pieces labeled as 107. Shoulder straps pads labeled as 106.
Figure 12A:
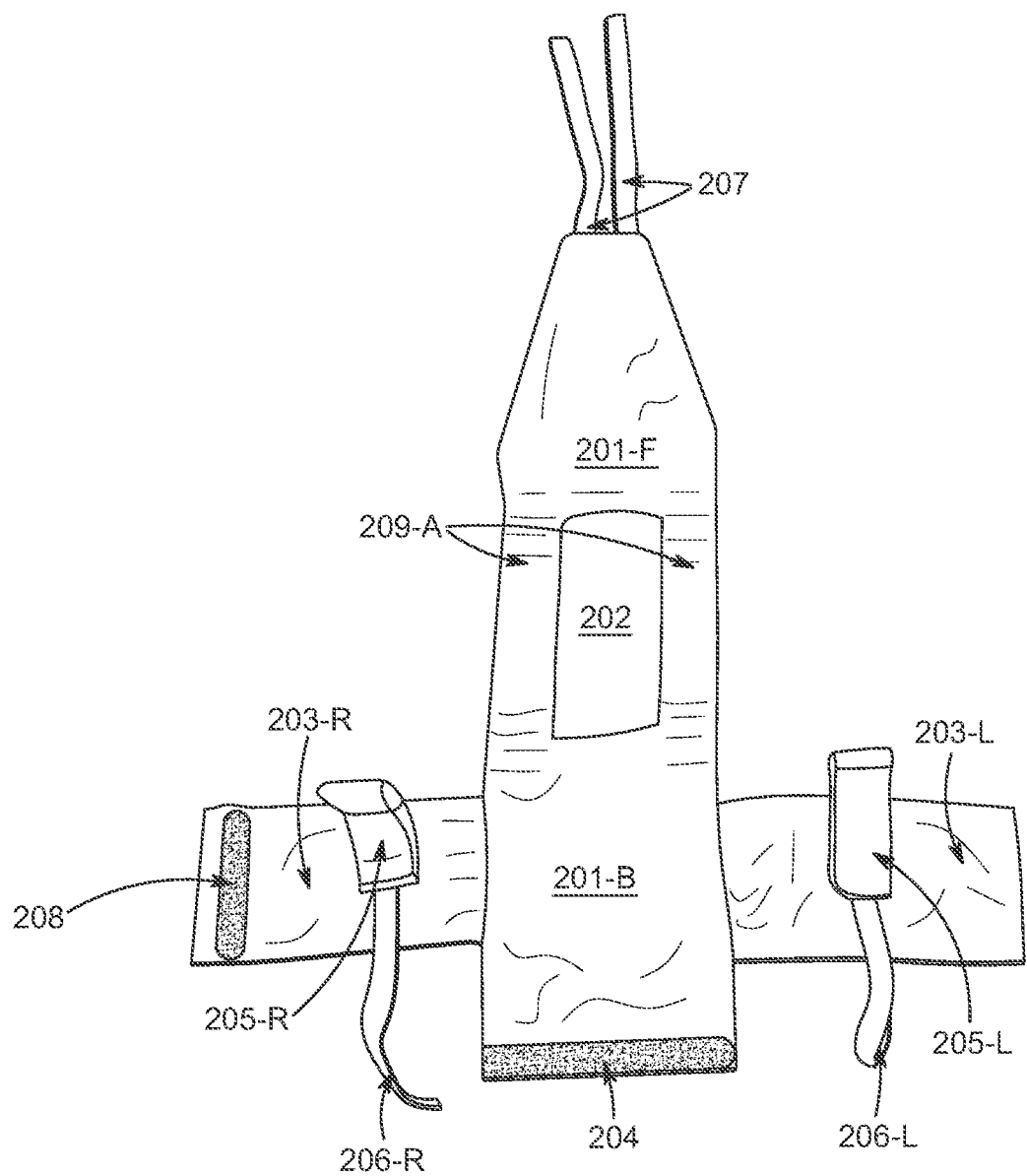
FIG. 12-A provides an overview of the inner side of the overhead jacket with hand restraints attached. 201-F is the frontal part of the jacket that will be applied to patient's anterior trunk. 201-B is the back part of the jacket that patient's back will rest over. 202 is the jacket gap to allow for patient's head and neck to get through the jacket. 203-R and 203-L are the jacket arms where 203-R is the right arm and 203-L is the left arm. 204 is jacket's attachment to the posterior jaw of the wedge. 205 is hand restraint where 205-R is right hand restraint and 205-L is left hand restraint. 206 is hand restraint strap where 206-R is right hand restraint strap and 206-L is left hand restraint strap. 207 identifies shoulder straps. 208 is the hook of the right jacket arm to be attached to the loop located at the back of the left jacket arm at time of application. 209-A is padded jacket shoulders.
Figure 12B:
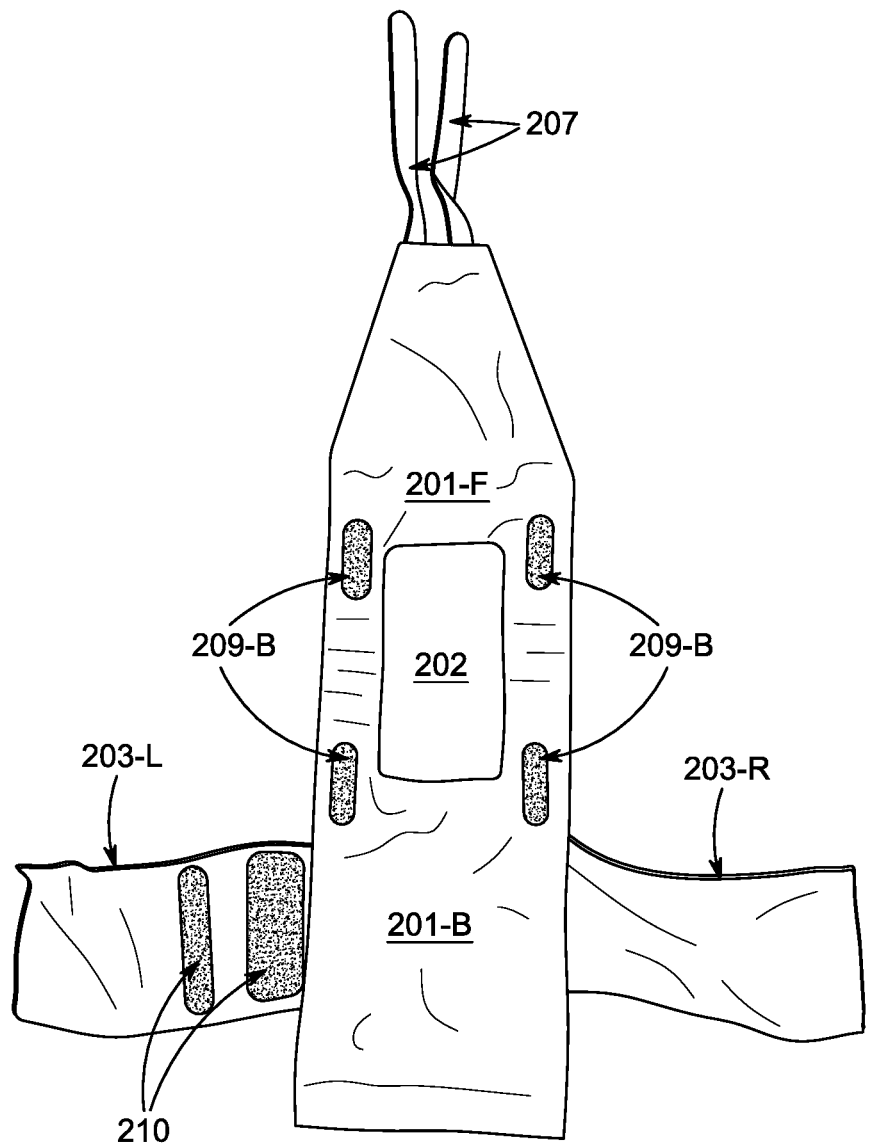
Figure 13A:
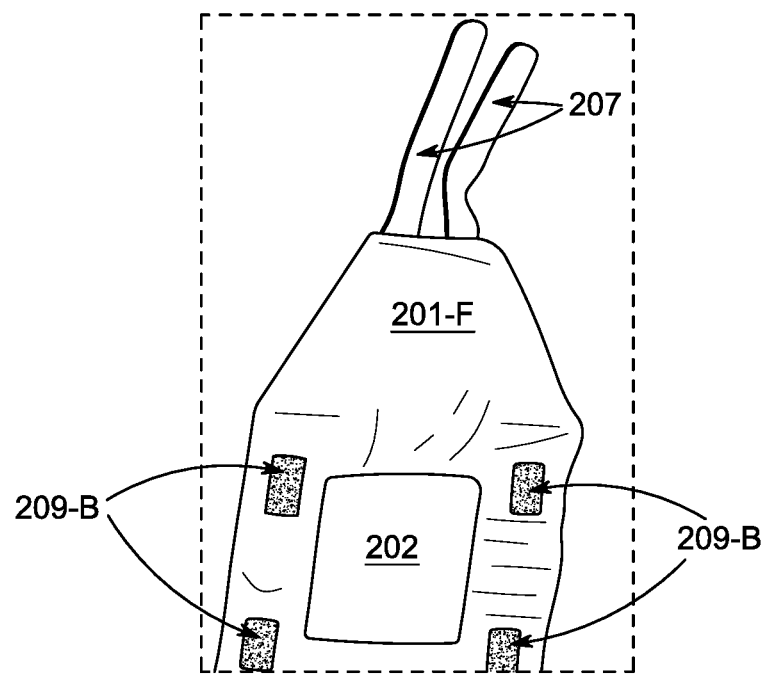
FIG. 13-A provides a close view of the overhead jacket frontal part which shows full length of 201-F which is the part that will be applied over patient's frontal trunk and will be attached to the anterior jaw of the wedge via 207 which are the shoulder straps. 207 will finally be attached to 209-B which are the hooks on the back side of jacket shoulders to secure the wedge to the patient.
Figure 13B:
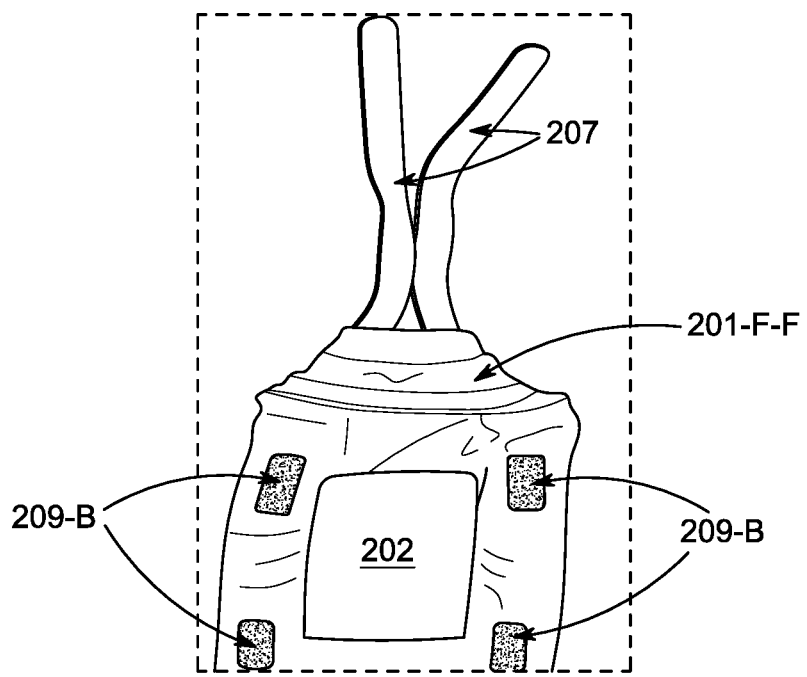
Figure 14A:
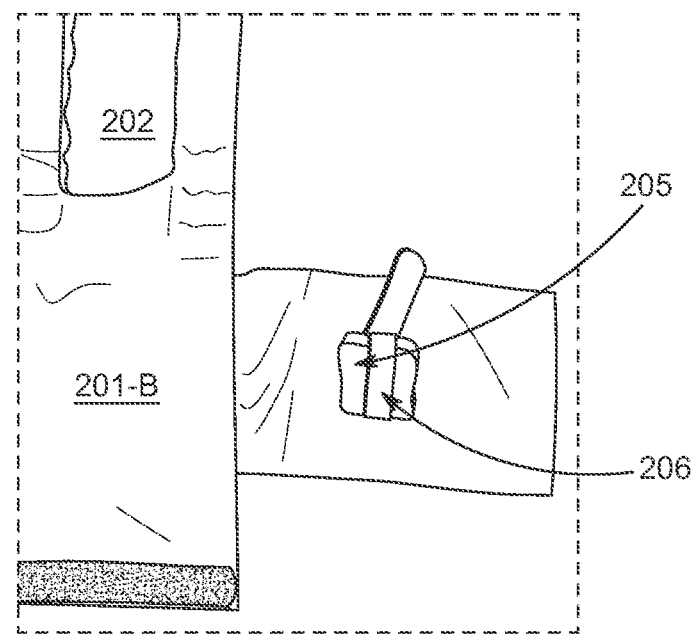
FIG. 14-A provides a close view of the overhead jacket at the level of jacket arm where a closed hand restraint is attached. 201-B is the back part of the jacket that patient's back will rest over. 202 is the overhead jacket gap to allow for patient's head and neck to get through the jacket. 205 is the closed hand restraint. 206 is the secured hand restraint strap.
Figure 14B:
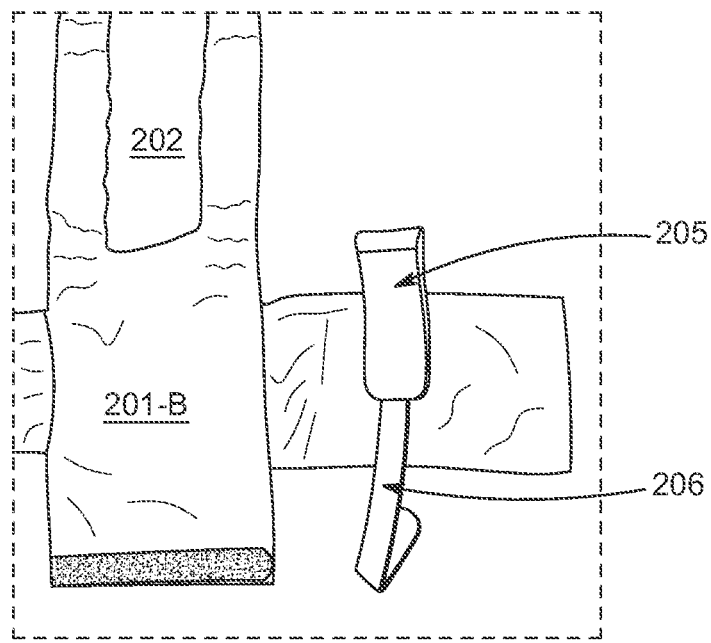

The invention provides a lithotomy-positioning, restraining or holding device that is safe, sanitary, easy to use, and suitable for repeated use, especially for catheterization of a pediatric patient. The device comprises a splint portion that positions, holds, or restrains the legs in a lithotomy position when worn by a patient. The splint is typically ring-shaped or toroid-shaped and is bent at an acute angle forming an anterior jaw which fits between patient's legs and the posterior jaw which fits behind and helps support a patient's back. The anterior jaw is smaller than the posterior jaw. Two bent or looped portions at the corners, joints, or intersections of the jaws help position and support the legs of the patient in a lithotomy position Embodiments of the invention include but are not limited to the following embodiments.

A device comprising a substantially wedge-shaped toroidal splint having an anterior and a posterior jaw, and at least one shoulder attachment for securing the lower wedge-shaped splint to the lower body; wherein the posterior jaw of the frame is configured to fit around the back of a patient and the anterior jaw of the frame is configured to fit between the patient's legs and place the patient's hips in flexion and abduction or into a lithotomy position; wherein the at least one shoulder attachment fits over the patient's shoulders and attached at its opposite ends to the anterior and posterior jaws. The toroid may contain concave or convex indentations or lengths of thinner or thicker padding to provide a complementary surface to a leg, back or other body part in contact with the splint to comfortably seat the legs and attach the device to the patient.

The device as disclosed herein may be used with male and female patients in need of procedures, examination, or treatments in which placement into a lithotomy position is desired. The lithotomy position is a medical term referring to a common position for surgical procedures and medical examinations involving the pelvis and lower abdomen, as well as a common position for childbirth. The lithotomy position involves the positioning of an individual's feet above or at the same level as the hips (often in stirrups), with the perineum positioned at the edge of an examination table. The position is perhaps most recognizable as the often used position for childbirth where the patient is laid on her back with knees bent, positioned above the hips, and spread apart through the use of stirrups.

Preferably, the device is designed and configured for use with a pediatric patient, such as a subject with a body weight between 3 to 15.5 kg whom is expected to be noncompliant, incompetent, or difficult patient or for patients having movement disorders that can interfere with procedures or examination of the perineal or anorectal areas. Wedge and shoulder straps size can be further modified to fit patients whose body weight is more than 15.5 kg.

It typically is secured and fitted to a patient by adjusting suspender-like shoulder straps or adjusting over-the-head jacket attachments to secure the device to the patient. The shoulder attachments attach directly or indirectly to the toroid, for example, one end of an attachment to the anterior jaw of the toroid and the other end of the attachment to the posterior jaw of the toroid. In some embodiments, the attachments may be to the joint or lateral loops between, or formed by, the anterior and posterior jaws. The straps or other shoulder attachments may attach directly to the toroid or its jaws, for example, by looping or being tied or secured around a jaw, or indirectly via fittings, clips, clasps, zippers, Velcro-like material, buttons, or other mechanical attachments that attach to the toroid and to the straps or shoulder attachments.

The splint as well as the shoulder attachment(s) may be padded for patient comfort and to provide a good or comfortable fit. The splint, shoulder attachment, and any other elements of the device such as hand, wrist, foot or ankle restraints may be padded.

The splint, shoulder attachment(s) and other elements may be waterproof or may be covered with a waterproof coating or layer. In some embodiments, the device or one or more of its components is washable. In other embodiments, the device is covered by a disposable covering which may be sanitarily replaced for each repeated use.

Typically, this device is configured for positioning and holding a patient into a lithotomy position where the hips are restrained and avoids placing a person into a less desirable frog leg position, where the legs are aligned at the same level as the hips, or a position in which the hips are not restrained thus providing an open field for medical observation or procedures. By placing a patient into a lithotomy position it provides free access to a procedure field without distraction or obstruction caused by lower limbs because in this position the lower limbs are positioned upwards and outwards.

Moreover, the device as disclosed herein does not require attachment to the patient's bed or surroundings, only attachment to the patient. This is highly advantageous because it allows a patient to be rapidly repositioned in case of an emergency, for example, a vomiting patient can be rapidly repositioned from a supine to a lateral position, thus preventing aspiration of vomit or gastric contents.

The device as disclosed herein also provides support for the back and pelvic area unlike other devices that do not support pelvic area and which do adequately restrain hip movement when a patient is put into a lithotomy position.

The device as disclosed herein is typically independent of medical attachments, such as catheters, catheter guides or holders, tubes for removal of urine or padding that covers the urethral area and obstructs the observation or operating field.

Shoulder attachment may be straps, suspenders, vest, jacket or other garment that serves to connect the splint to the patient's body.

The posterior and anterior jaws of the wedge-shaped splint may be bent or shaped into a fixed angular position or can be adjustable, for example, the wedge may include a locking hinge, ratchet, or other mechanism to produce a particular angle between the jaws and permit adjustment of the angle for patients of different sizes. The jaw may fit a wide range of body weights. In some embodiments, the angle of the wedge may range from 20, 25, 30, 35, 40, 45, 50, 55, 60, 65, 70, 75, 80, 85 to 90° (or any intermediate angle), for use in producing a lithotomy position, preferably at an acute angle ranging from about 30 to 60°. Advantageously, the positioning wedge angle is about 45°.

The splint typically comprises a back rest that is about 12-14 inches in size on the outside and about 11 to 13 inches on the inside; a front jaw that is about 4.5 to 6.5 inches on the outside and about 2.5 to 4.5 inches on the inside; and a thigh support that is about 10-13 inches on the outside and about 8-10 inches on the inside; wherein said outside measurements are larger than the inside measurements. The splint is typically made of a durable, substantially rigid, and non-brittle material, such as plastic or reinforced plastic. A plastic component may contain particulate, fibrous or wire reinforcements. Preferably, the splint has some flexibility and resiliency so as to make it durable and not easily cracked or broken.

In some embodiments, the core of the toroid is made out of a moldable medical grade plastic material such as a moldable thermoplastic that is malleable when heated and rigid at body or room temperature. Air splint can be used as a material to make the toroid. Air splint is a type of material that will not need padding; it is easy to disinfect and is disposable.

In a preferred embodiment, the device is composed of three separate hard plastic pieces; which are molded and attached to each other and then cooled to create a single hard frame. Afterwards, the frame is wrapped with a soft padding for the patient's comfort.

The wedge-shaped splint has a strong support frame and fits securely to the patient providing stability to the back, hips and pelvic area and frontal sides of the patient's body. The splint is placed close to patient's hips which secure them in flexion and abduction positions throughout the procedure; unlike other devices where movement of the hips is not restrained. The high frontal curve of the splint prevents trunk movement and places the patient's knees and feet outside and far away from the perineal and anorectal areas thus giving free access to these areas for medical exams and medical and surgical procedures to be completed without a risk of harming the patient or getting distracted or obstructed by lower limbs in the procedure field. Preferably the wedge or splint may comprise a nonstick antibacterial splinting material such as ORFIBRACE™ or comprise air splint.

Padding either on or around the splint, on the shoulder attachments, or on other attachments to the device, such as restraints, is selected for the comfort of the patient as well as in view of providing a snug fit. The padding may be smooth or textured. Examples of padding, or batting, materials include plastics and rubbers, such as foamed plastic, sponge rubbers, natural fibers or synthetic fibers, or mixtures of these with other materials. In some embodiments, the padding may be foam, such as memory foam, or cushioning such as that used in pillows. In one embodiment, the padding is inflatable and can be inflated with air or water. The same or different type of padding used for the splint may be used for the shoulder attachments or wrist and ankle restraints or other parts of the device.

The device, or any part of it, may be coated with a waterproof coating or may be covered by a waterproof, water-repellant, or stain resistant material. A water-proof or water-resistant material is typically selected to prevent fluids from penetrating it and contaminating the padding material covering the splint or other parts of the device. Such materials include water-proof plastics, waterproof or water-resistant textiles having hydrostatic ratings ranging from 1,500, 3,000, 5,000, 10,000, 15,000 to 20,000; or chemical coatings such as perfluorooctane sulfonate (PFOS) or perfluorobutanesulfonic acid (PFBS). Other covering materials include polyethylene, latex, or nitrile or other materials that avoid contamination between multiple uses of the device. A sanitary, disposable covering provides protection against soiling during use of the splint, for example, by passage of urine or stool during a procedure, thus allowing for sanitary reuse of the device.

Figure 15A:
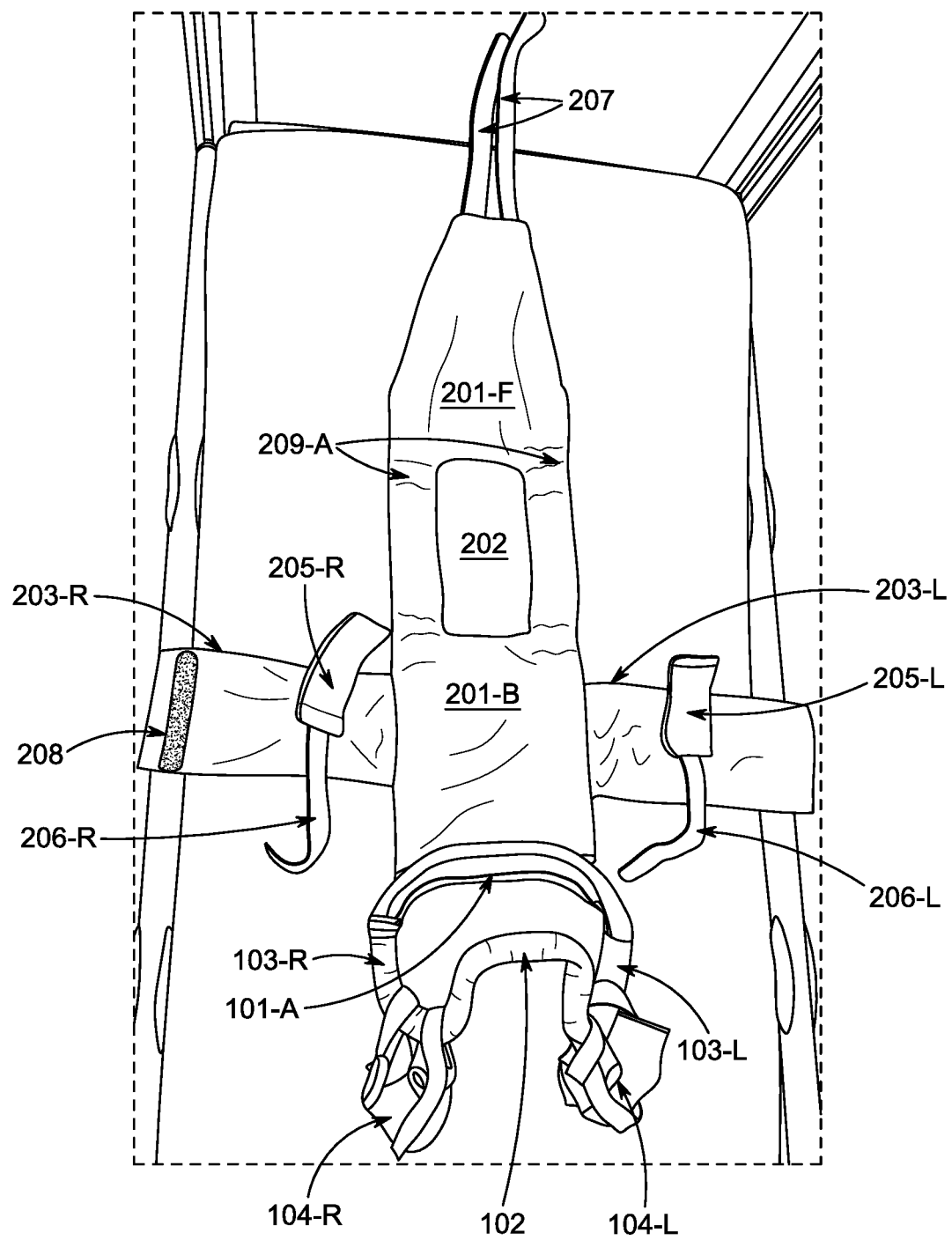
FIG. 15-A shows an overview of the device where the overhead jacket is attached to the outer side of the posterior jaw of the wedge. 101-A is the internal side of the posterior jaw of the wedge where patient's back will lie on. 102 is the anterior jaw of the wedge, 103-R is the right angulated side of the wedge where the right thigh will be placed on and 103-L is the left angulated side of the wedge where the left thigh will be placed on. Attached to 103-L is 104-L which is the left ankle restraint to demonstrate the placement of the ankle restraint in this embodiment to the angulated side of the wedge. Attached to 103-R is 104-R which is the right ankle restraint to demonstrate the placement of the ankle restraint in this embodiment to the angulated side of the wedge. 201-F is the frontal part of the overhead jacket that will be applied to patient's anterior trunk. 201-B is the back part of the overhead jacket that patient's back will rest over. 202 is the jacket gap to allow for patient's head and neck to get through the jacket. 203-R and 203-L are the jacket arms where 203-R is the right arm and 203-L is the left arm. 205-R is the open right hand restraint and 205-L is the open left hand restraint. 206-R is right hand restraint strap and 206-L is left hand restraint strap. 207 is shoulder straps. 208 is the hook of right jacket arm to be attached to the loop at the back side of the left jacket arm at time of application. 209-A is the padded jacket shoulders.
Figure 16:
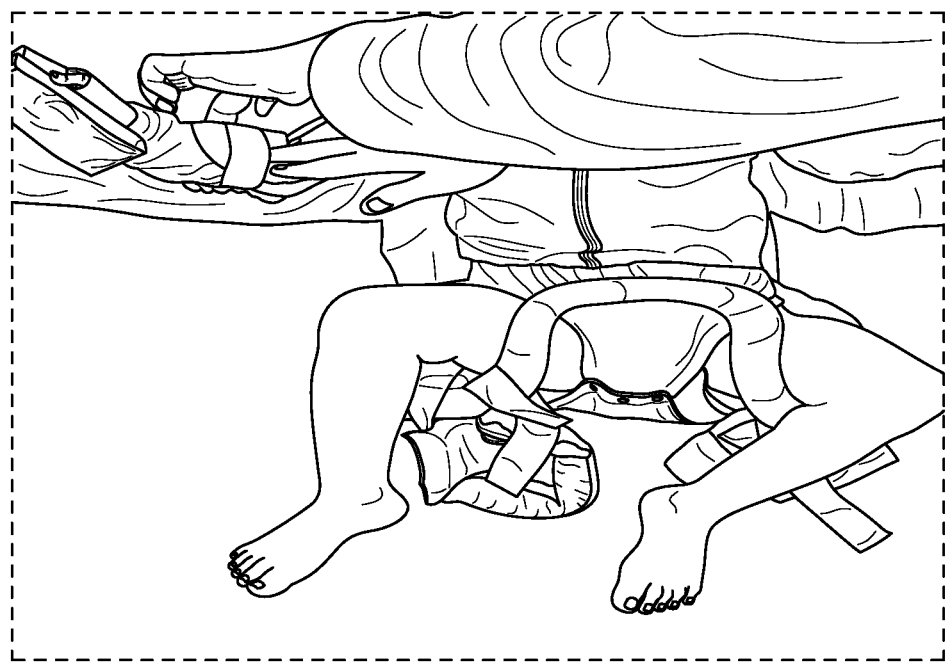
FIGS. 16 to 26 show the steps of device application on a pediatric patient.
Figure 17:
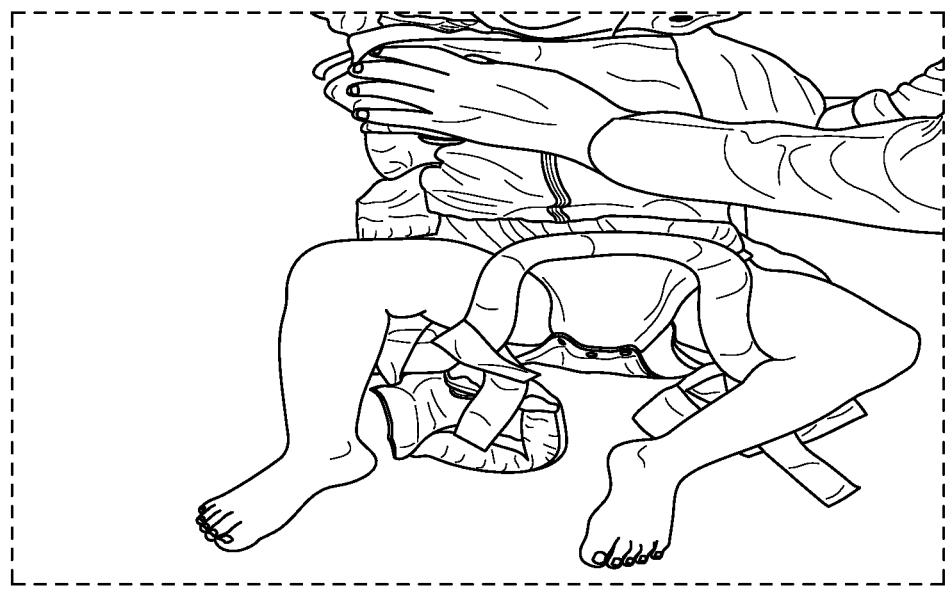
Figure 18:
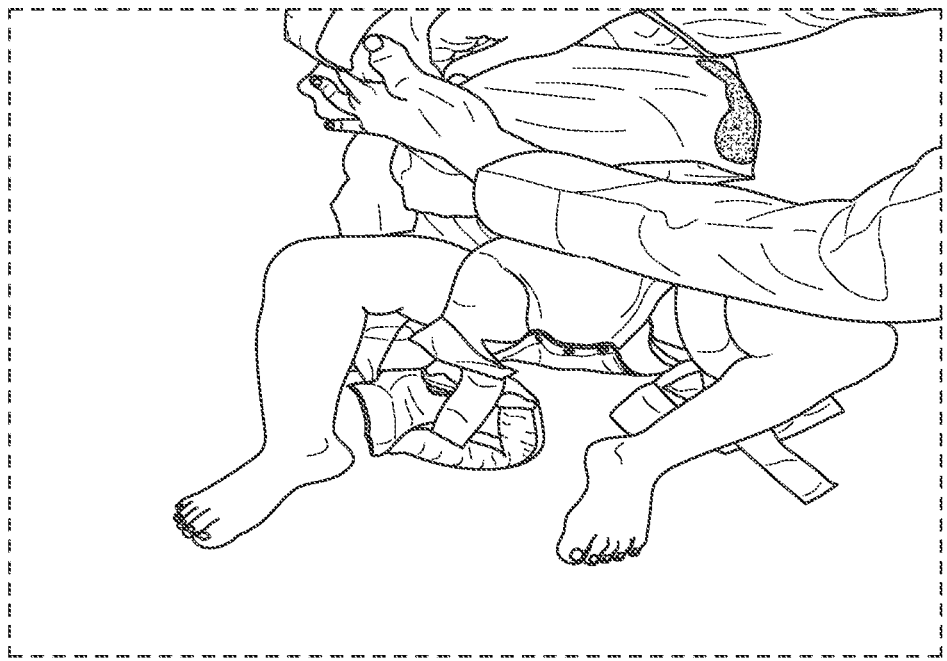
Figure 19:
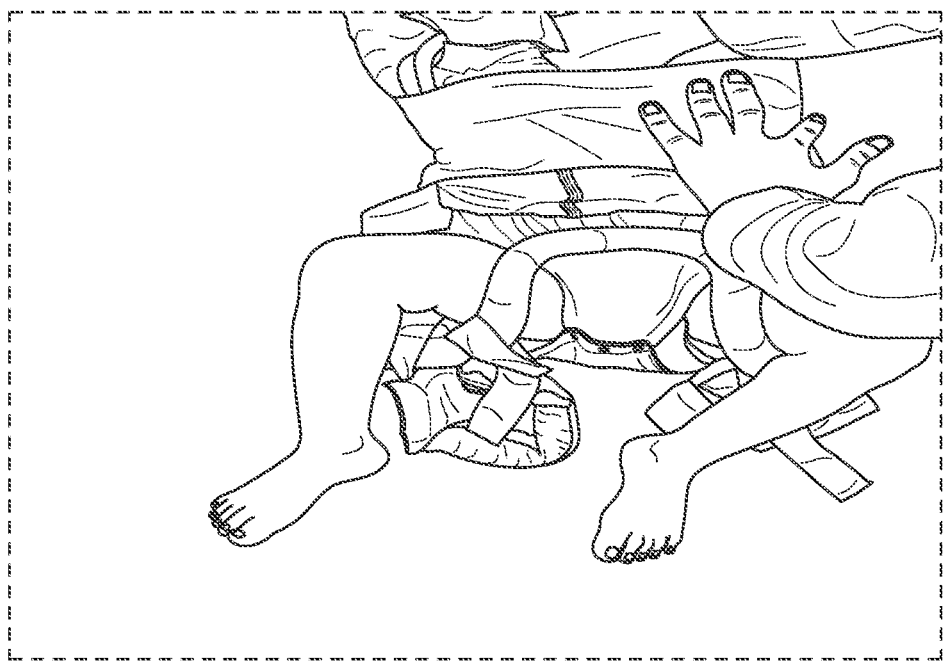
Figure 20:
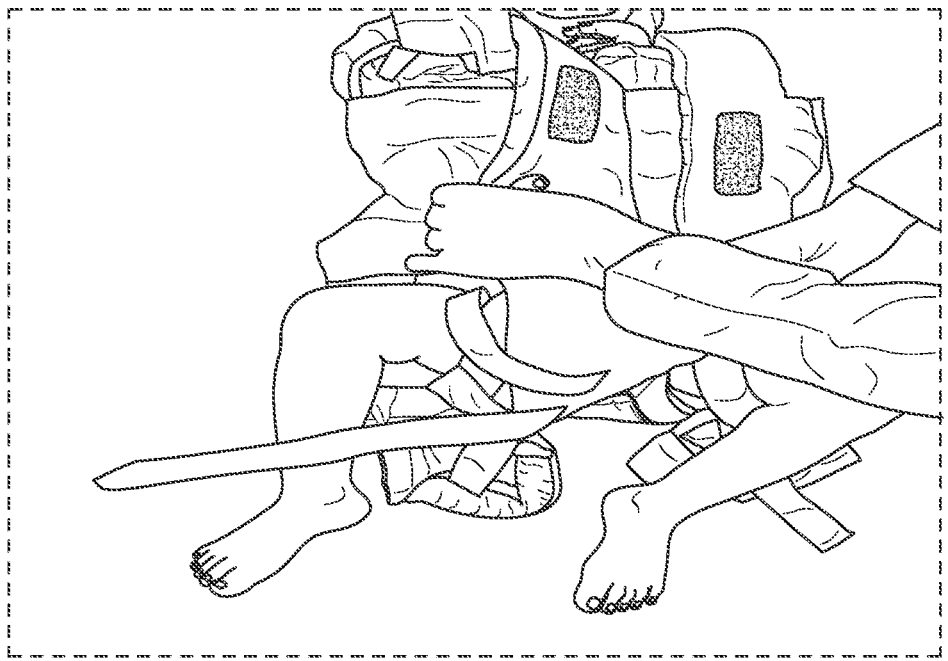
Figure 21:
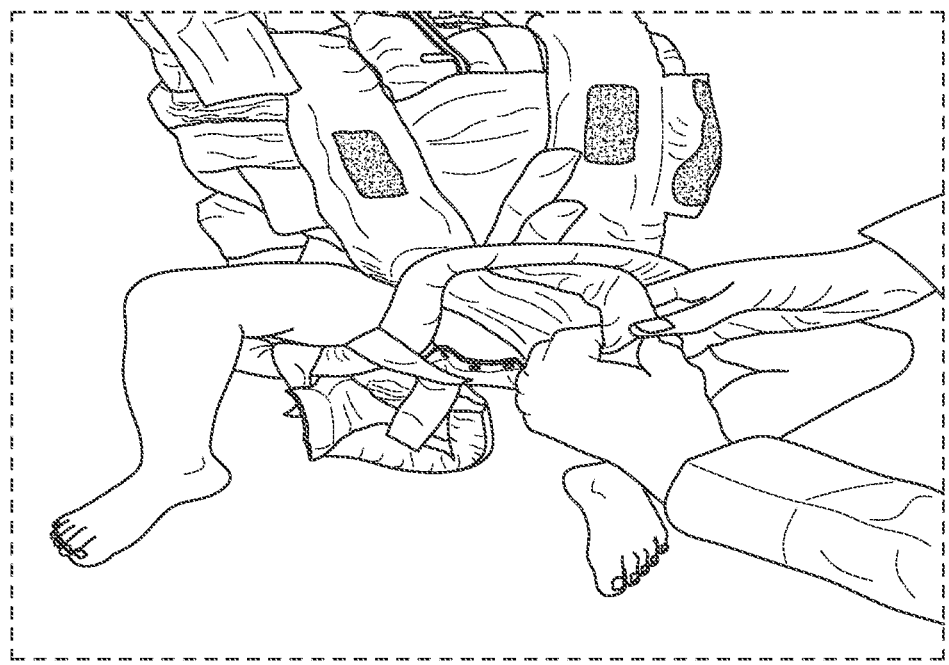
Figure 22:
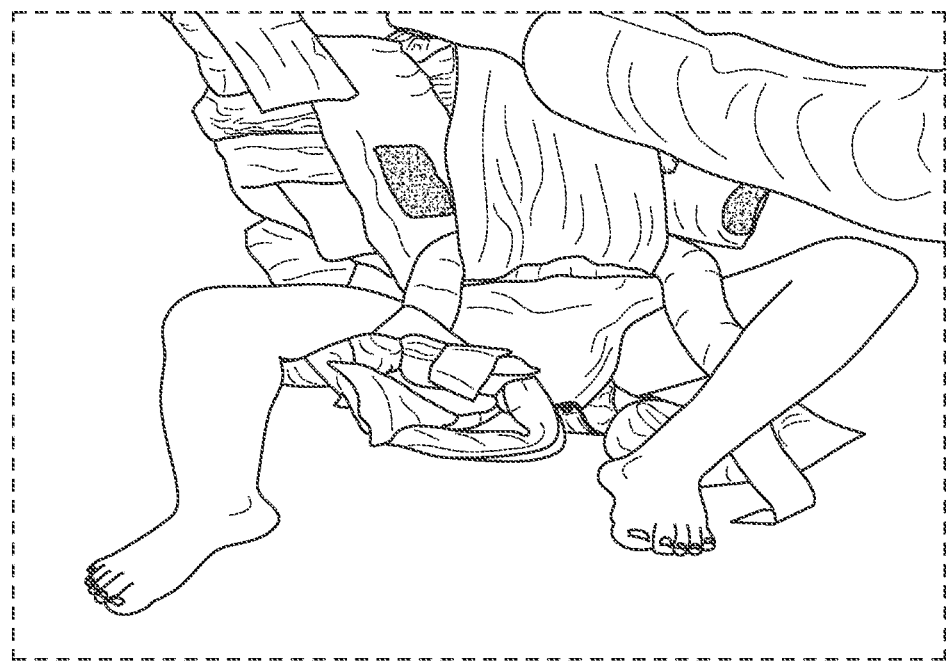
Figure 23:
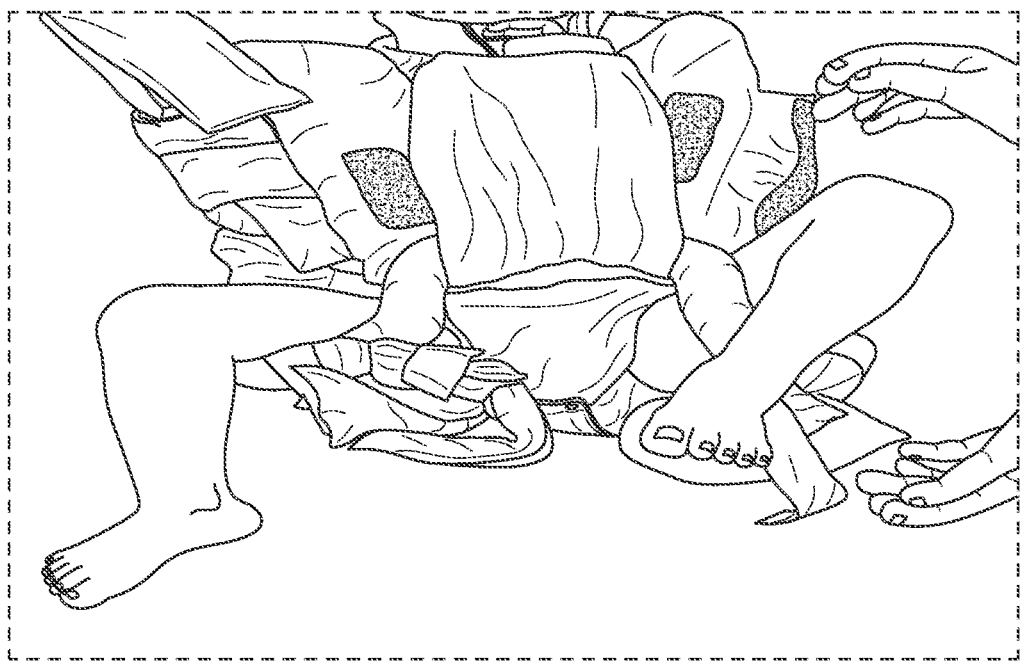
Figure 24:
Figure 25:
Figure 26:

The shoulder attachment or attachments are selected to secure the splint to the patient and comfortably place the patient into a lithotomy position. Examples of such attachments include shoulder straps, a shoulder harness, and an over-the-head vest, jacket, or tunic. In one embodiment the shoulder attachments comprises two straps, one for each shoulder like suspenders. In another embodiment, the shoulder attachment is an over-the-head jacket or vest as shown by FIG. 15. The shoulder attachment may be attachable or integrated with a belt or sash or hand or wrist restraints to help immobilize the arms and hands. The belt or sash may wrap around the torso and secure the arms next to the body, for example, with Velcro-like fasteners, zippers, buttons or other conventional fasteners.

Figure 27:
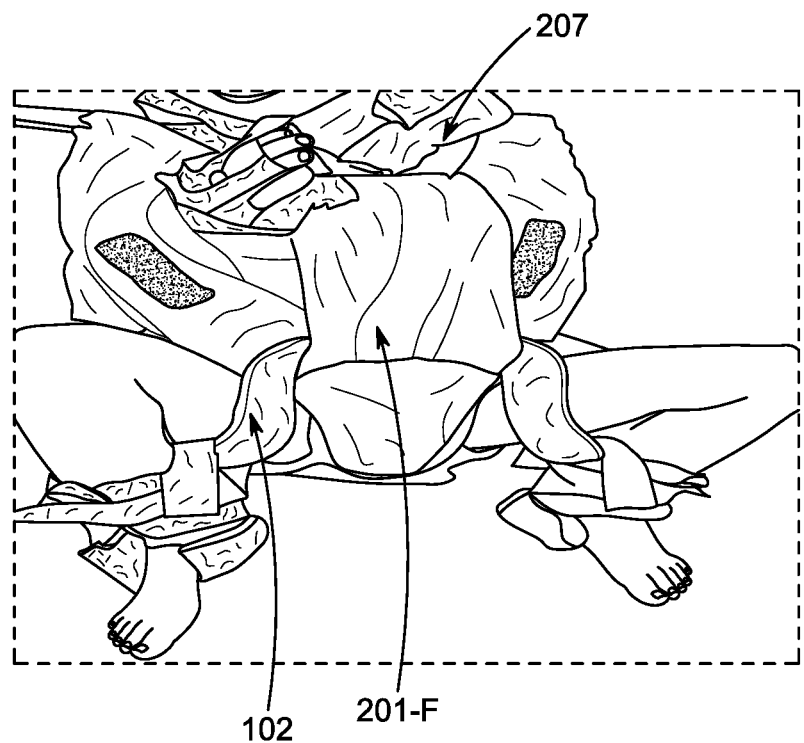
FIG. 27 shows the final look of the device on a pediatric patient after complete application. 102 is the anterior jaw of the wedge and 201-F is the anterior part of the overhead jacket/vest and 207 is the shoulder straps.
Figure 28:
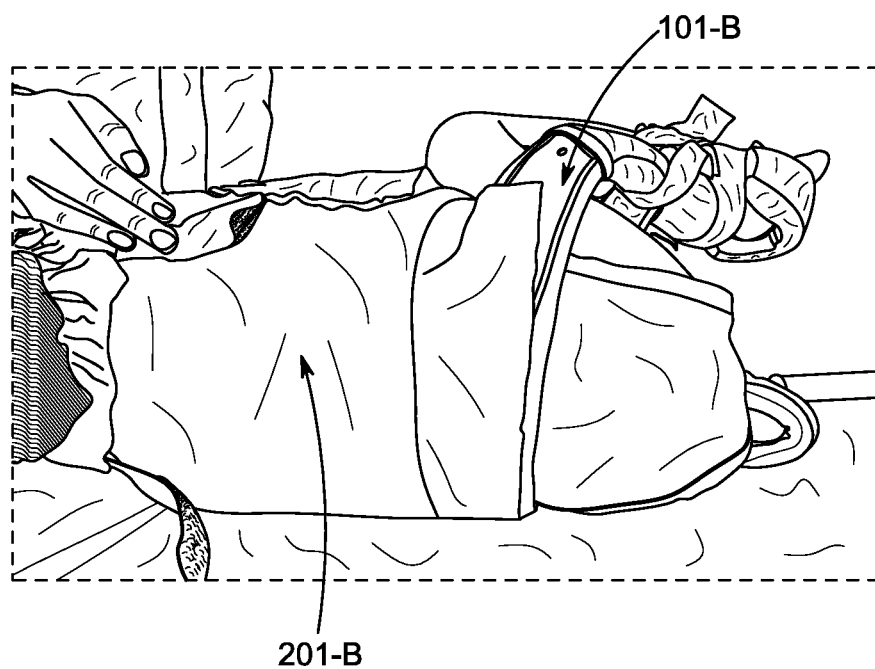
FIG. 28 shows the back side of the device while applied on a pediatric patient. The patient in this figure is put to the side while the device is applied. 201-B is the back part of the overhead jacket that is attached at its lower end to 101-B which is the outer side of the posterior jaw of the wedge via hook and loop.
Figure 29:
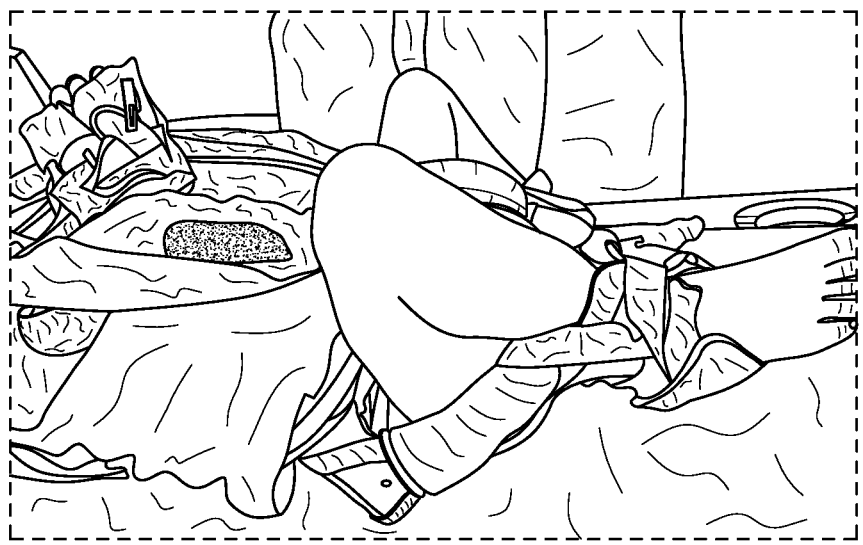
FIG. 29 shows a side view of the device while applied on a pediatric patient.
Figure 30:
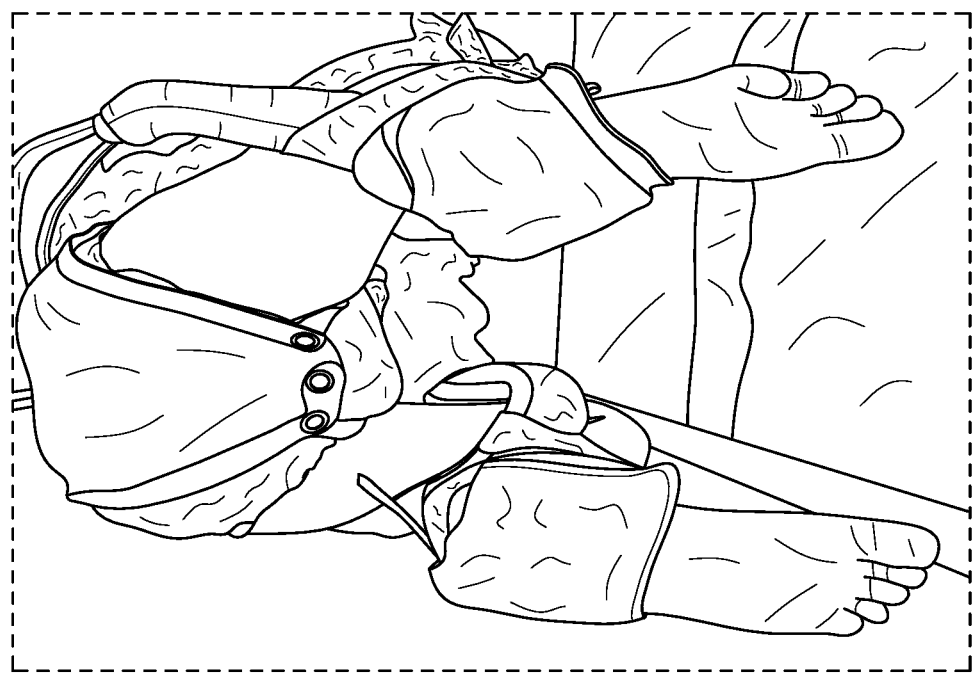
FIG. 30 shows downward view of the device while applied to a pediatric patient and the patient is put to the side.

The over-the-head jacket or vest is directly or indirectly attached to the wedge-shaped toroid or to its jaws. The jacket or vest typically comprises a long portion, which comprises a hole through which the patient's head fits, and forms a front side and back side when worn. The front and back sides are respectively attached near the patient's waist or hips to the wedge-shaped toroid splint typically to the respective anterior and posterior jaws of the splint. The length of the jacket or vest is approximately twice the distance from the patient's shoulders to waist or hips, for example, about 50, 60, 70, 80, 90 to 100 cm long and about 25, 30, 35, 40, or 50 cm wide. As depicted by FIG. 15, the overhead jacket drapes over the front of the patient's torso when worn by the patient via hole 202. The rear or posterior part of this jacket or vest 201-B is attached to the posterior jaw of the splint 101-B as demonstrated in FIG. 28. The front part 201-F of the overhead jacket or vest is secured to the splint via straps 207 as demonstrated in FIG. 27. As shown in FIG. 15-A, wings, sashes or arms 203-R and 203-L are the side part of the overhead jacket and when the vest or jacket is worn over the head will be wrapped around the patient to secure the arms next to the torso. In one embodiment each wing is about 25 to 50 cm in length. The jacket or vest may also have wrist/hand restraints 205-R and 205-L or ankle/foot restraints 104-R and 104-L as depicted by FIG. 15-A. Preferably, the back side of the jacket or vest is directly or removably attached to the posterior jaw of the splint and the front side is tied to the anterior jaw of the splint. The approximate dimensions ±10% of an embodiment of the jacket or vest are shown by FIG. 15-B. Thus such a jacket or vest may have the following measurements: arm cover length: 14 cm; lower back length: 8 cm; jacket width: 25 cm; complete Arm cover width: 82 cm; each side width: 28.5 cm; head pocket length: 21 cm; head pocket width: 13 cm; inside padding length: 21 cm; and strap length: 50 cm.

The shoulder attachments are typically adjustable, for example, with slide adjusters or bar slides, buckles, and/or be made of elastic material. Typically, the shoulder attachments attach at one end to the posterior jaw of the splint, loop over the shoulders, and attach at the other end to the anterior jaw of the splint. In some embodiments, they may attach to the joint between, or intersection of, the posterior and anterior jaws of the splint.

The shoulder attachments may attach to the splint with ties, snaps, magnetic fasteners, hook-and-loop connectors, or other mechanical connectors or fasteners, or with adhesive connectors such as Velcro®-style fasteners. The splint, shoulder attachment(s) and other parts of the device such as restraints or padding, may be integrated with the splint and other parts of the device or can separable from it to permit replacement of a damaged, missized, or dirty component. For example, shoulder straps may be permanently attached at one end to the splint and have a free end which can be looped over the shoulders and attached to the splint. In other embodiments, shoulder straps used for one patient, may be replaced with shoulder straps properly sized for a different patient.

The shoulder straps are used to secure the patient in a lithotomy position and to prevent the wedge-shaped splint from sliding out or away from its intended position on the patient. In another embodiment, the shoulder attachments constitute a one piece overhead jacket for better outlook which may be padded for comfort and prevent undue pressure or abrasion in areas of contact with a patient.

Wrist and ankle straps can be added to ensure patient's hands and feet will not interfere with a procedure field. Hand, wrist, leg and ankle restraints may be made of the same materials as the shoulder attachments and may be padded and have fasteners to secure them to the limbs, such as those used to secure the shoulder attachments. Such restraints may be attached to the splint or to the shoulder attachment.

Another embodiment of the invention is directed to a method for making the device as disclosed herein that includes molding a minimum of three pieces of splint material to fit patient weight between 3-15.5 kg in a configuration such that the molded article fits around a patient's back and thighs to form a wedge-shaped toroid splint having an anterior and posterior jaw; attaching each end of a strap or other wearable material, respectively, to the posterior and anterior jaws of the splint thereby producing a shoulder attachment, such as a suspender-like attachment or a vest or jacket-like attachment; and padding the splint and/or shoulder attachment. Three pieces of the splint material are respectively molded to fit around the patient's back and each thigh, and joined together to form a wedge-shaped toroidal splint having anterior and posterior jaws, which may have an internal angle ranging from 20 to 90°. Prior to fitting the device to a patient, weight and waist measurement should be considered.

Another embodiment of the invention is directed to a method for placing a patient in a lithotomy position that involves positioning the patient in a supine position inside the posterior and anterior jaws of the device as disclosed herein, so as to place the legs of the patient in flexion and abduction and expose the perineal area of the patient which is defined as the area between the symphysis pubis and coccyx in both male and female patients. The lithotomy position provides the best exposure of the perineal area. It can be advantageously used for a pediatric patient in need of placement into a lithotomy position to perform examination of the perineal or anorectal areas or to perform any of the following surgical procedures: circumcision, cystoscopy, proctoscopy, anoplasty, rectal biopsy, cliteroplasty, vaginoplasty, labioplasty, perianal abscess, fistulectomy, certain type of sagittal anorectoplasty and hemorrhoids surgeries. Preferably the back side of the splint is padded for comfort to avoid pressure sores that may develop during prolonged procedures and surgeries. The device as disclosed herein also facilitates examination of external genitalia of pediatric patients by gynecologists.

In some preferred embodiments, the patient is a pediatric patient in need of urinary catheterization, and the method further comprises catheterizing the patient once placed in the lithotomy position. The device can be used for urethral catheter insertion and when an indwelling catheter is later needed to be removed. The device as disclosed herein is advantageously used to ensure lithotomy positioning of pediatric patients to facilitate catheter insertion through the urethra.

Inserting a catheter through the urethra is one of the most common procedures done in the pediatric field. Some of the indications for catheter insertion through the urethra in pediatric patients are urine sample collection, urine output monitoring, emptying the urinary bladder and performing certain diagnostic procedures like micturating cystourethrogram or urodynamic study. This procedure carries stress related to the risks of injuries that may occur during it.

The injury may happen either during positioning of the child while performing this invasive procedure or during the catheter insertion itself where the risk of injury increases if the child is not maintained in stable position during the procedure. One example of iatrogenic injury related to positioning is fractures in the lower limbs especially in children with fragile bones which are related to excessive force applied by personnel during lithotomy positioning in an uncooperative patient during the procedure.

In addition, pediatric patients diagnosed with neurogenic bladder are sent home to continue on intermittent catheterization through the urethra that is done 4-6 times per day to empty the urinary bladder. The caregivers of neurogenic bladder patients are trained by competent health care workers to do catheter insertion through the urethra for the child. However, the majority of pediatric patients are uncooperative when it comes to performing such a procedure. Hence, conventionally at least one person is needed to ensure stability of positioning while the other one is performing the catheterization of urethra. The device as disclosed herein advantageously permits such procedures by one person.

Other indications to use this device are to ensure lithotomy positioning for the following surgical procedures: circumcision, cystoscopy, proctoscopy, anoplasty, rectal biopsy, cliteroplasty, vaginoplasty, labioplasty, treatment of a perianal abscess, fistulectomy, certain type of sagittal anorectoplasty or hemorrhoid surgery. The back side of the splint can be padded for comfort and to avoid pressure sores development during prolonged procedures and surgeries.

Contraindications to use this device is any bone fracture involving the spine, pelvis, hip or femur. Other contraindications are contractures or any limitation of movement of the hip joint or any open wounds involving the back or pelvic areas.

Example 1

Method for Making a Lithotomy Splint

Preferably, the method disclosed herein produces a one-size device that fits a wide range of body weights, such as a body weights between 3 and 15.5 kg. It is possible to custom design and make the device for a particular class of patients or patient, for example by customizing the device for patients weighing under 3 kg or over 15.5 kg.

A main body of the splint is sized through measurements of a patient's back from pelvic crest to pelvic crest and thigh circumference divided by about a factor of 2.

The core of the splint is fabricated by positioning the patient is a supine position with bilateral knees in 90 degree flexion, and bilateral hips in 90 degree flexion and abduction.

A first stage of fabrication comprises cutting a splint material into three sheets and molding them. One piece of splint was shaped around the patient's back in a flat position (to make the back rest) and the other two other pieces were molded around patient's thighs and attached together (to make the front jaw).

A second stage of fabrication comprises washing the splint to cool and harden it and then fitting and marking the cooled splint for adjustment.

A third stage comprises applying a thin layer of padding to avoid the production of pressure points during use and attachment and length adjustment of the shoulder straps. Alternatively, the shoulder straps are replaced by an overhead jacket which is adjusted for length. The material used to fabricate the core is ideally known to have high rigidity, high resistance to stretch and hold moderate memory. The material is easy to handle and control during molding and fitting as it does not stick onto bandage during molding. The material is very strong as it holds its shape against increase tone. Suggested materials are non-stick or antimicrobial materials such as ORFIBRACE™ or materials like air splint.

Example 2

Pediatric Urinary Catheterization Using the Splint by a Single Medical Worker

Weight and appropriate measurements of a pediatric patient are taken and a lithotomy splint as disclosed herein is custom fit to the pediatric patient.

A medical caregiver inserts the anterior jaw of the splint between the patient's legs and the posterior jaw behind the back and the shoulder straps of the device are secured over the patient's shoulders, thus placing the patient securely in a lithotomy position.

Once secured to the lithotomy splint apparatus, the exterior area around the urethra is cleaned, a lubricant is applied, and a pediatric catheter is gently inserted.

To facilitate safe removal of a catheter, a pediatric patient may be placed into the device during catheter removal.

In order to apply the positioning splint, first, the jacket or shoulder straps are attached to the posterior jaw of the wedge splint and then spread over the bed or a flat surface as in FIG. 15-A.

Second, the health care provider or patient's care giver place the child over the laid out shoulder straps or overhead jacket.

Third, child's legs will be lift up from ankles with one hand while maintaining 90 degrees hip and knees flexion. Afterwards, the health care giver slides the patient into the wedge splint to position the anterior jaw between patient's legs while resting patient's back on the posterior jaw of the wedge splint. This maneuver is as easy as applying a diaper onto a child.

Finally, the shoulder straps of the overhead jacket are looped over the anterior jaw of the wedge splint and attached finally to the hook on the jacket shoulders to secure it in place.

FIGS. 16-26 depict the steps of applying the device to a patient by a single caregiver.

Some of the advantages of the device disclosed herein are that it is easily applied and removed from a patient. It may be applied by a single person to stabilize a patient in a lithotomy position and easily removed by a single person once a procedure is finished. The device is typically attached only to the patient and not to the patient's bed or medical surfaces, such as an operating table. This provides the advantage of instantly changing the patient's position during a procedure whenever needed, for example after an urgent indication such as when patient is about to vomit and is at risk of aspiration of gastric content. Another benefit is that when the device is used for an anxious and scared patient, he or she can be put on the lap of the care giver while the device is attached to them to give them chance to calm down while preparing for exam or procedure. Another benefit, is that the device disclosed herein is light weight and easily stored between times of use and can be disinfected and used for different patients. Advantageously, a single device can fit patients having a wide range of weights and the shoulder straps or overhead jacket can be adjustable in length to fit a wide range of patient sizes. The device is versatile and cost effective and can be used in a variety of different types of examinations, procedures and surgeries requiring that the patient be placed in a lithotomy position. The construction of the device avoids the risk of pressure sores when applied to a patient for a short time and the device can be padded during prolonged procedures or surgeries for additional comfort.

Terminology.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

All publications and patent applications mentioned in this specification are hereby incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A device suitable for holding a pediatric patient in a lithotomy position, comprising:
a wedge-shaped toroidal splint formed from a continuous narrow strip of a rigid material bent to form an anterior jaw and a posterior jaw, and an adjustable shoulder attachment having a length which is adjustable to fit over the shoulders and securely fit the splint to the patient's body, and ankle or foot restraints attached to the wedge-shaped toroidal splint, wherein
the posterior jaw of the wedge-shaped toroidal splint is formed from a portion of the continuous narrow strip of the rigid material which is substantially flattened and is configured to fit around the back of the patient and the anterior jaw of the wedge-shaped toroidal splint is formed from a portion of the continuous narrow strip of the rigid material which is substantially rounded and is configured to first curve below a patient's thighs and then curve upward and forward to form an inverted U-shape which fits between the patient's legs and place the patient's hips in flexion and abduction;
the device has a ratio of a posterior jaw size to an anterior jaw size of 1.85:1 to 3.11:1;
the shoulder attachment fits over the patient's shoulders and is attached at opposite ends to the anterior and posterior jaws; and
the device is suitable for holding a pediatric patient in a lithotomy position in which the patient is laid on their back with their feet positioned above the level of the hips.

2. The device of claim 1, wherein the device comprises padding disposed on at least one selected from the group consisting of the wedge-shaped toroidal splint and the shoulder attachment.

3. The device of claim 1, wherein the wedge-shaped toroidal splint has a wedge angle that fits a wide range of body weights.

4. The device of claim 1, wherein the wedge-shaped toroidal splint has a wedge angle that ranges from about 20 to 90 degrees thereby forming the anterior and posterior jaws.

5. The device of claim 1, wherein the posterior jaw of the wedge-shaped toroidal splint comprises a back rest that is 12 to 14 inches in size on a back rest outside and 11 to 13 inches on a back rest inside; wherein the anterior jaw of the wedge-shaped toroidal splint is 4.5 to 6.5 inches on an anterior jaw outside and 2.5 to 4.5 inches on an anterior jaw inside; and wherein the wedge-shaped toroidal splint comprises a thigh support that is 10 to 13 inches on a thigh support outside and 8 to 10 inches on a thigh support inside; wherein said outside measurements are larger than the inside measurements.

6. The device of claim 1, wherein the rigid material comprises plastic or air splint.

7. The device of claim 1, further comprising
   a shoulder attachment or splint padding made of a material comprising foam plastic, sponge, natural fibers, or synthetic fibers.

8. The device of claim 1, further comprising a waterproof covering.

9. The device of claim 1, wherein the shoulder attachment is adjustable in length.

10. The device of claim 1, wherein the shoulder attachment comprises shoulder straps that attach at each of its ends to the posterior and anterior jaws of the wedge-shaped toroidal splint.

11. The device of claim 1, wherein the shoulder attachment comprises an overhead jacket or vest.

12. The device of claim 1, further comprising a belt configured to wrap around the patient's torso and configured to restrain the arms of the patient.

* * * * *